US010466183B2

(12) United States Patent
Seetho et al.

(10) Patent No.: US 10,466,183 B2
(45) Date of Patent: Nov. 5, 2019

(54) SYSTEM-INDEPENDENT CHARACTERIZATION OF MATERIALS USING DUAL-ENERGY COMPUTED TOMOGRAPHY

(71) Applicant: Lawrence Livermore National Security, LLC, Livermore, CA (US)

(72) Inventors: Isaac Seetho, Hayward, CA (US); Maurice B. Aufderheide, Livermore, CA (US); Stephen G. Azevedo, Livermore, CA (US); William D. Brown, Antioch, CA (US); Kyle Champley, Walnut Creek, CA (US); Daniel Schneberk, Ripon, CA (US); G. Patrick Roberson, Livermore, CA (US); Jeffrey S. Kallman, Pleasanton, CA (US); Harry E. Martz, Jr., Livermore, CA (US); Jerel A. Smith, Boulder Creek, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 15/339,821

(22) Filed: Oct. 31, 2016

(65) Prior Publication Data

US 2018/0120241 A1 May 3, 2018

(51) Int. Cl.
*G01N 23/046* (2018.01)
*G01N 23/083* (2018.01)
*G06T 11/00* (2006.01)

(52) U.S. Cl.
CPC ......... *G01N 23/046* (2013.01); *G01N 23/083* (2013.01); *G06T 11/005* (2013.01);
(Continued)

(58) Field of Classification Search
None
See application file for complete search history.

(56) References Cited

U.S. PATENT DOCUMENTS

| 2012/0148133 | A1* | 6/2012 | Chen | A61B 6/032 |
| | | | | 382/131 |
| 2018/0078233 | A1* | 3/2018 | Jin | A61B 6/585 |

OTHER PUBLICATIONS

Alvarez, et al., "Energy Selective Reconstructions in X-ray Computerized Tomography," Physics in Medicine and Biology, vol. 21, No. 5, pp. 733-744, 1976.

(Continued)

*Primary Examiner* — Hoon K Song
(74) *Attorney, Agent, or Firm* — Perkins Coie LLP

(57) ABSTRACT

A system for characterizing the material of an object scanned via a dual-energy computed tomography scanner is provided. The system generates photoelectric and Compton sinograms based on a photoelectric-Compton decomposition of low-energy and high-energy sinograms generated from the scan and based on a scanner spectral response model. The system generates a Compton volume with Compton attenuation coefficients from the Compton sinogram and a photoelectric volume with photoelectric attenuation coefficients from the photoelectric sinogram. The system generates an estimated effective atomic number for a voxel and an estimated electron density for the voxel from the Compton attenuation coefficient and photoelectric coefficient for the voxel and scanner-specific parameters. The system then characterizes the material within the voxel based on the estimated effective atomic number and estimated electron density for the voxel. This information can be used to provide a mapping of known effective atomic numbers and known electron densities to known materials.

30 Claims, 4 Drawing Sheets

(52) U.S. Cl.
CPC .. *G01N 2223/063* (2013.01); *G01N 2223/423* (2013.01); *G06T 2207/10081* (2013.01); *G06T 2211/408* (2013.01); *G06T 2211/416* (2013.01)

(56) References Cited

OTHER PUBLICATIONS

Bond, et al., "ZeCalc Algorithm Details," LLNL Tech. Rep. LLNL-TR-609327, Jan. 2013, 13 pages.

Iovea, et al., "High Accuracy X-ray Dual-Energy Experiments and Non-Rotational Tomography Algorithm for Explosives Detection Technique in Luggage Control," Int. Symp. Digital Industrial Radiology and Computed Tomography, Lyon, France, Jun. 2007, 9 pages.

Mayneord, M. V., "The Significance of the Reontgen," Acta of the International Union Against Cancer, vol. ii, pp. 271, 1937.

Poludniowski, et al., "SpekCalc: A Prograph to Calculate Photo Spectra from Tungsten Anode X-Ray Tubes," Phys. Med. Biol., 54:N433-8, Sep. 2009.

Smith, J. A., "Ze:an Effective Atomic Number for Polychromatic X-ray Transmission," LLNL-JRNL-640273, Jul. 3, 2013, 17 pages.

Ying, et al., "Dual energy computed tomography for explosive detection," J. X-Ray Sci. and Tech., vol. 14, pp. 235-356, 2006.

\* cited by examiner

SYSTEM-INDEPENDENT CHARACTERIZATION OF MATERIALS USING DUAL-ENERGY COMPUTED TOMOGRAPHY

STATEMENT REGARDING FEDERALLY SPONSORED RESEARCH

The United States Government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND

X-ray Computed Tomography ("CT") is a technique that noninvasively generates cross-sectional images of the linear attenuation coefficients ("LACs") of materials in an object of interest. X-ray CT has been used extensively in medical, industrial, and security applications, such as generating cutaway images of a brain, detecting flaws in a piston, or observing internals of baggage at an airport. The LAC is a measure of the distance-dependent attenuation of X-rays as they pass through a certain material and has units of inverse length (e.g., per centimeter). Typically, X-ray CT systems employ an X-ray source, which emits a pencil, fan, or cone beam of photons through an object with an initial intensity. A single element, linear, or area array X-ray detector measures the final intensities of the X-ray beams that pass through the object and impinge on the detector pixels. For X-ray CT, the source and detector are positioned at various angles relative to the object and measurements of the final intensity at each angle are collected. The set of measurements for each angle is referred to as a projection. Various techniques may be used to collect measurements at different angles relative to the object, for example, the source and detector may be stationary and the object may be moved, the object may be stationary and the source and detector may be moved, and multiple stationary sources and detectors may be positioned at different angles. CT algorithms then reconstruct, from the collection of measurements, a 3D image of the object that specifies the LAC for each volume element ("voxel") within the volume of the object. Cross-sectional images are generated from the 3D image.

There is strong interest in the security field in efforts to extend CT technology to help characterize physical and chemical characteristics of objects being scanned. For example, for airport security, it would be helpful to determine whether an object found in checked baggage contains an explosive material. While X-rays are ill-suited for determining specific molecular structure and composition, X-ray CT technology can be used to generate a high-resolution estimate of both the electron density ($\rho_e$) and effective atomic number ($Z_{eff}$) of compounds in each voxel within an object. Conventional CT employs a single source that generates X-rays over a certain spectral energy distruibution. The two independent parameters $\rho_e$ and $Z_{eff}$, however, cannot be determined from a single-spectrum measurement, such as the measurements of a single-energy-source CT scanner. So, Dual-Energy CT ("DECT") has been used to enable these estimates.

DECT generates measurements for two photon spectral energy distributions. Because there are two sets of partially orthogonal measurements, the values for $\rho_e$ and $Z_{eff}$ can be estimated. DECT typically employs either voltage switching or a sandwich detector. With voltage switching, the X-ray source voltage and source filtration are modulated to different levels to generate low- and high-energy photon spectral energy distributions. With a sandwich detector, a filtering material is placed between two detector elements in the same X-ray beam line. The first detector in the beam sees an initial photon spectral energy distribution with a lower energy bias relative to the spectral distribution observed at the second detector due to attenuation by the additional filtration. DECT generates a low-energy LAC volume specifying the LAC ($\mu_{low}$) of the low-energy spectrum in each voxel, and a high-energy LAC volume specifying the LAC ($\mu_{high}$) of the high-energy spectrum in each voxel. The electron density ($\rho_e$) is roughly proportional to $\mu_{high}$, and the effective atomic number ($Z_{eff}$) can be approximated as a function of the ratio of $\mu_{low}$ over $\mu_{high}$. These approximations for calculating ($\rho_e$) and ($Z_{eff}$ demonstrate poor accuracy. In addition, these approximations do not compensate for differences in spectral responses between scanners or spectral drift due to wear in a single scanner.

DETAILED DESCRIPTION

Figure 1:
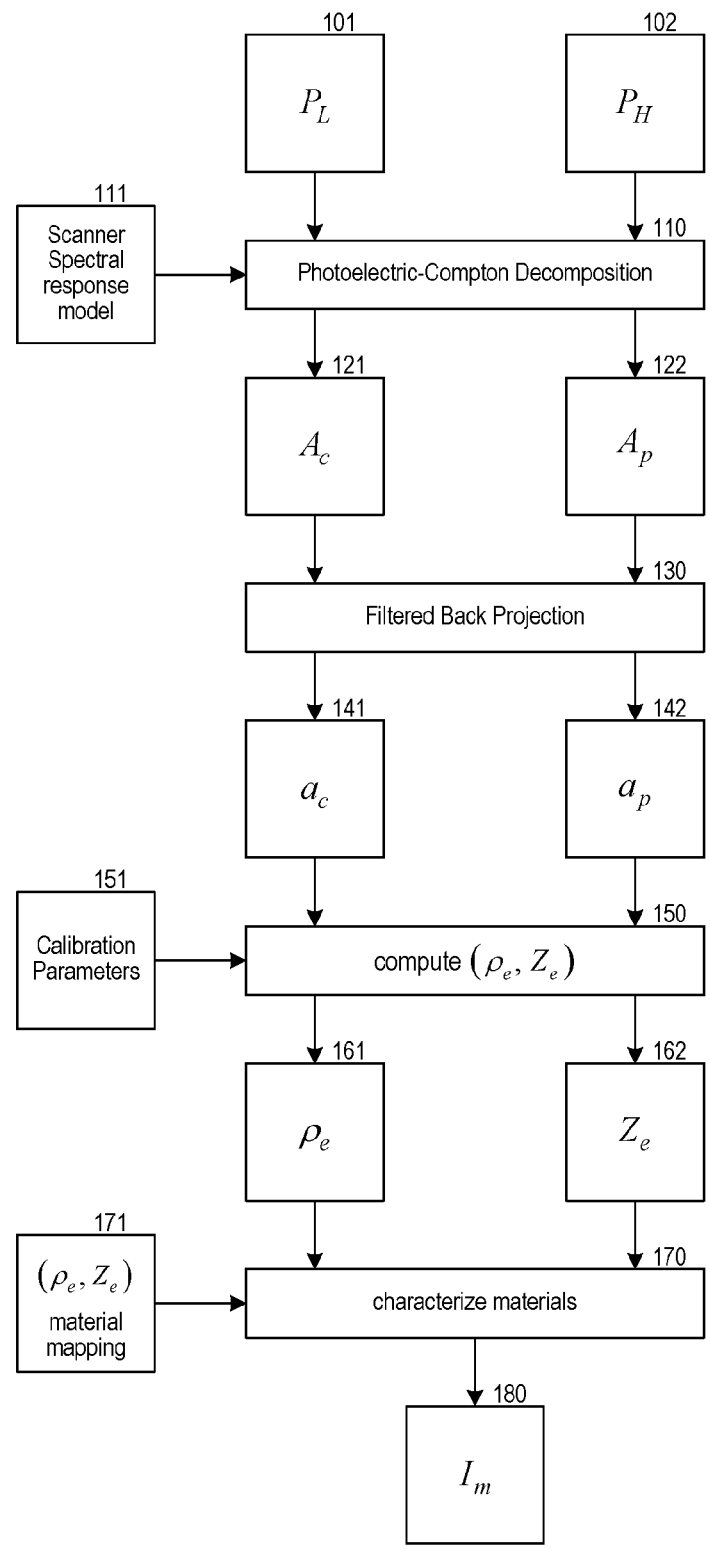
FIG. 1 is a flow diagram that illustrates the processing of the System-Independent ($\rho_e$, $Z_e$) ("SIRZ") system in some embodiments.

A method and system are provided that generates a system-independent measure of electron density ($\rho_e$) and X-ray cross section-derived definition of effective atomic number ($Z_e$) for characterizing a material scanned via a DECT scanner. In some embodiments, a SIRZ system receives a low-energy sinogram ($P_L$) and a high-energy sinogram ($P_H$) based on a scan of the material using a DECT scanner. The sinograms represent an X-ray transform for the projection data collected by the DECT scanner. The SIRZ system then generates a photoelectric sinogram ($A_p$) and a Compton sinogram ($A_c$) based on a photoelectric-Compton decomposition (PCD) of the low-energy sinogram and the high-energy sinogram, and based on a low- and high-energy spectral response estimates for the scanner. The spectral responses may be generated by creating a model for the scanner and applying the model to different energy bands. The SIRZ system then generates a photoelectric volume ($a_p$) indicating a photoelectric attenuation coefficient for each voxel within a volume (i.e., 3D image) that represents the material based on the photoelectric sinogram. The SIRZ system also generates a Compton volume ($a_c$) indicating a Compton attenuation coefficient for each voxel within the volume that represents the material based on the Compton sinogram. For each voxel of the volume, the SIRZ system generates an estimated electron density ($\rho_e$) based on the Compton attenuation coefficient for the voxel and a scanner-specific electron density calibration. For each voxel of the volume, the SIRZ system also generates an estimated effective atomic number ($Z_e$) based on a ratio of the photoelectric attenuation coefficient and the Compton attenuation coefficient and a scanner-specific effective atomic-number calibration. For each voxel element, the SIRZ system then identifies the material based on a combination of the estimated electron density and the estimated effective atomic number. To characterize the material, the SIRZ system employs a feature space ($\rho_e$, $Z_e$), which reflects the X-ray absorption properties of the material in an energy range and effective atomic-number range of interest. That feature space can be used to associate the scanned material to potential known threat materials. Since the feature space is directly associated with X-ray cross sections, the feature space can reflect material properties with results that are less dependent on the spectral responses of a particular scanner, which is far more accurate than prior techniques.

In some embodiments, the SIRZ system calculates the estimated electron density ($\rho_e$) for a voxel based on the Compton attenuation coefficient and a parameter that is calibrated to the scanner. Compton X-ray attenuation is directly proportional to the electron density of a material, whereas the mass density of a material is not directly related to X-ray attenuation. The mass density of a known material, however, can be calculated from weight and volume measurements. The electron density of a known material can be calculated from the mass densities of its constituent elements by the following equation:

$$\rho_e = \sum_{i=1}^{N} \frac{Z_i}{A_i} \rho$$

where $A_i$ is the atomic mass and $Z_i$ is the atomic number for element i, and $\rho$ is the mass density of the material. Since electron density is directly proportional to the Compton attenuation coefficient, the SIRZ system estimates the electron density by the following equation:

$$\hat{\rho}_e = K a_c$$

where K is a scanner-specific electron density calibration parameter that is determined based on scans of reference materials.

In some embodiments, the SIRZ system calculates the estimated effective atomic number ($Z_e$) for a voxel based on a ratio of the photoelectric attenuation coefficient, the Compton attenuation coefficient and parameters that are calibrated to the scanner. The SIRZ system estimates the effective atomic number by the following equation:

$$\hat{Z}_e = k \left( \frac{a_p}{a_c} \right)^{1/n}$$

where k and n are scanner-specific effective atomic number calibration parameters based on scans of reference materials. A tool, referred to as ZeCalc, can be used to determine values for $\rho_e$ and $Z_e$ for known materials. (See Bond, K. C., Smith, J. A., Treuer, J. N., Azevedo, S. G., Kallman, J. S., and. Martz Jr., H. E., "ZeCalc Algorithm Details," LLNL Tech. Rep., LLNL-TR-609327, January 2013.)

To characterize the materials within a target object, the SIRZ system calculates ($\rho_e$, $Z_e$) based on projection data of the target object generated by a DECT scanner. The SIRZ system inputs the low-energy sinograms $P_L$ and the high-energy sinograms $P_H$ of the logarithmic projections generated by the DECT scanner. The SIRZ system decomposes the sinograms into their photoelectric and Compton components ($A_p$, $A_c$) factoring in the spectral response model of the scanner, generates photoelectric and Compton values ($a_p$, $a_c$) from the reconstructed photoelectric and Compton components, and generates ($\rho_e$, $Z_e$) for each voxel of the volume of the target object factoring in calibration parameters for the scanner. The $P_L$ and $P_H$ sinograms are related to the photoelectric and Compton components by the following approximate equations:

$$P_L = -\ln\{\int S_L(E)\exp[-(E^{-3})A_p - f_{KN}(E)A_c]dE\} + \ln\int S_L(E)dE$$

$$P_H = -\ln\{\int S_H(E)\exp[-(E^{-3})A_p - f_{KN}(E)A_c]dE\} + \ln\int S_H(E)dE$$

where $A_p$ and $A_c$ are line integrals of the photoelectric and Compton attenuation coefficients, $S_L$ and $S_H$ are the low-energy and high-energy X-ray scanner spectral responses (including both the source and detector) as a function of energy, E is the X-ray energy, and $f_{KN}$ is the Klein-Nishina formula for free-electron Compton scattering as follows:

$$f_{KN}(E) = \frac{1+\alpha}{\alpha^2}\left[\frac{2(1+\alpha)}{1+2\alpha} - \frac{1}{\alpha}\ln(1+2\alpha)\right] + \frac{1}{2\alpha}\ln(1+2\alpha) - \frac{1+3\alpha}{(1+2\alpha)^2}$$

where alpha is $E/m_e$ and $m_e$ is the rest mass of the electron. The SIRZ system solves for $A_p$ and $A_c$ using a constrained minimization method that employs the scanner spectral responses generated using a spectral response model of the scanner. The SIRZ system may initially compute each $A_p$ and $A_c$ projection value using a two-dimensional Newton-Raphson technique with non-negativity constraints on the solution. If a low-energy projection or a high-energy projection value is less than or equal to zero (suggesting the absence of an attenuating region), the SIRZ system sets the resulting photoelectric and Compton projection values to zero. When the optimization yields a negative photoelectric or Compton projection value, which describes a non-physical outcome, the SIRZ system may perform a Gauss-Newton optimization under the added constraint that either $A_p$ or $A_c$ is zero, which guarantees the complementary value to be positive. The resulting pair that minimizes the mean squared error between back-computed projection values and observed projection values is preserved. The SIRZ system then reconstructs the photoelectric attenuation coefficient volume $a_p$ and the Compton attenuation coefficient volume $a_c$ using a filtered back projection ("FBP") technique or other tomographic reconstruction technique.

In some embodiments, the SIRZ system employs scanner spectral responses, $S_L$ and $S_H$, to generate $A_p$ and $A_c$. The scanner spectral responses are the product of the X-ray source spectrum, the detector spectral response for the low-energy spectra and the high-energy spectra, and the spectral transmission of any system filters or other components that lie between the source and detector. The SIRZ system may calculate the scanner spectral responses by, for example, generating a model of the detector using full electron-photon transport to simulate energy deposition in the detector. The model may be based on the materials and thicknesses through which the X-rays pass as specified by, for example, vendor-supplied specifications. The SIRZ system may use various software tools to generate the system spectral model. (See Iovea, M., Neagu, M., Duliu, O. G., and Mateiasi, G., "High Accuracy X-Ray Dual-Energy Experiments and Non-Rotational Tomography Algorithm for Explosives Detection Technique in Luggage Control," Int. Symp. Digital Industrial Radiology and Computed Tomography, Lyon, France, June 2007 and Poludniowski, G., Landry, G., DeBlois, F., Evans, P. M., and Verhaegen, F., "*SpekCalc*: A Program to Calculate Photon Spectra from Tungsten Anode X-Ray Tubes," Phys. Med. Biol, 54:N433-8, September 2009.) As vendor-supplied specifications may not account for all filtration components, the SIRZ system model may be adjusted to match estimated transmissions for a set of specimens with known values of $(\rho_e, Z_e)$ and sample thickness. If the transmissions do not closely match the experimentally measured transmissions for the specimens, the filtration components of the system response model can be adjusted until the transmissions match.

In some embodiments, the SIRZ system generates the calibration parameters for a scanner using reference materials. The SIRZ system may include the reference materials in each scan and generate the calibration parameters on a per-scan basis. Alternatively, the SIRZ system may periodically generate scans of the reference materials and generate calibration parameters to be used until the next scan of the reference materials. To generate the calibration parameters, the SIRZ system generates the $a_p$ and $a_c$ volumes for each reference material. The SIRZ then applies an optimization technique (e.g., a least square fit) to determine the parameters that produce the best fit for the reference materials from the $a_p$ and $a_c$ volumes to the $(\rho_e, Z_e)$ values.

FIG. 1 is a flow diagram that illustrates the processing of the SIRZ system in some embodiments. The SIRZ system 100 initially inputs low-energy sinogram $P_L$ 101 and high-energy sinogram $P_H$ 102 that are generated from a DECT scan of a target object. A photoelectric-Compton decomposition component 110 of the SIRZ system inputs the low-energy sinogram $P_L$ and the high-energy sinogram $P_H$ along with a scanner spectral response model 111 for the scanner and decomposes the low-energy sinogram $P_L$ and the high-energy sinogram $P_H$ into the corresponding Compton sinogram $A_c$ 121 and photoelectric sinogram $A_p$ 122. A filtered back projection component 130 of the SIRZ system inputs the Compton sinogram $A_c$ and the photoelectric sinogram $A_p$, and generates the corresponding Compton attenuation coefficient volume $a_c$ 141 and photoelectric attenuation coefficient volume $a_p$ 142 for the target object. A compute $(\rho_e, Z_e)$ component 150 inputs calibration parameters 151 for the scanner and the Compton attenuation coefficient volume $a_c$ and the photoelectric attenuation coefficient volume $a_p$ and calculates an electron density $\rho_e$ 161 and an effective atomic number $Z_e$ 162 for each voxel of the volume of the target object. After the SIRZ system outputs the electron density $\rho_e$ and effective atomic number $Z_e$, an identify materials component 170 inputs a mapping 171 of $(\rho_e, Z_e)$ to the corresponding materials and may input the electronic density $\rho_e$ and the effective atomic number $Z_e$ for each voxel, and identifies the material $I_m$ 180 in each voxel of the target object.

The computing systems on which the SIRZ system may be implemented may include a central processing unit, input devices, output devices (e.g., display devices and speakers), storage devices (e.g., memory and disk drives), network interfaces, graphics processing units, cellular radio link interfaces, and so on. The computing systems may include servers of a data center, massively parallel systems, FPGA (Field Programmable Gate Array) and/or ASIC (Application Specific Integrated Circuit) hardware, and so on. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on them or may be encoded with computer-executable instructions or logic that implements the SIRZ system. The data transmission media are used for transmitting data via transitory, propagating signals or carrier waves (e.g., electromagnetism) via a wired or wireless connection.

The SIRZ system may be described in the general context of computer-executable instructions, such as program modules and components, executed by one or more computers, processors, or other devices. Generally, program modules or components include routines, programs, objects, data structures, and so on that perform particular tasks or implement particular data types. Typically, the functionality of the program modules may be combined or distributed as desired in various embodiments. Aspects of the SIRZ system may be implemented in hardware using, for example, an application-specific integrated circuit ("ASIC").

Figure 2:
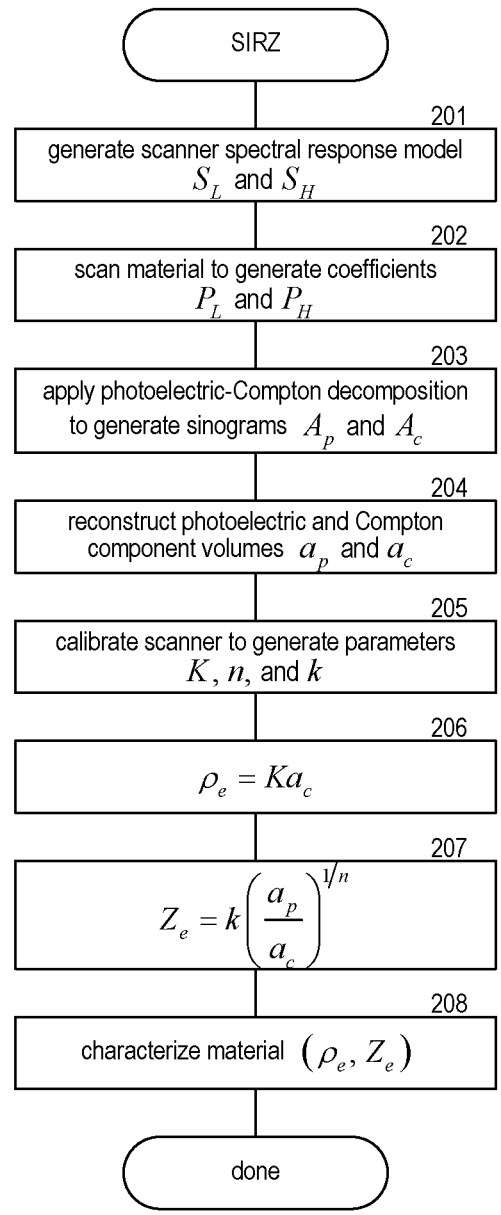
FIG. 2 is a flow diagram that illustrates the overall processing of the SIRZ system in some embodiments.

FIG. 2 is a flow diagram that illustrates the overall processing of the SIRZ system in some embodiments. The SIRZ system 200 identifies the material in each voxel of a volume representing a target object that is scanned. In block 201, the SIRZ system generates scanner spectral response models $S_L$ and $S_H$. In block 202, the SIRZ system scans the target object to generate measurements and to generate sinograms $P_L$ and $P_H$ from the measurements. In block 203, the SIRZ system applies a photoelectric-Compton decomposition to generate the sinograms $A_p$ and $A_c$ from the sinograms $P_L$ and $P_H$ and the scanner spectral response models. In block 204, the SIRZ system reconstructs a photoelectric component volume $a_p$ from the sinogram $A_p$ and a Compton component volume $a_c$ from the sinogram $A_c$. In block 205, the SIRZ system calibrates the scanner by generating calibration parameters K, n, and k from the reconstructed photoelectric attenuation component volume $a_p$ and Compton attenuation component volume $a_c$ derived from the scans of known reference materials. In block 206, the SIRZ system calculates the estimated electron density $\rho_e$ for each voxel. In block 207, the SIRZ system calculates the effective atomic number $Z_e$ for each voxel. In block 208, the SIRZ system assigns $(\rho_e, Z_e)$ values to characterize the material.

Figure 3:
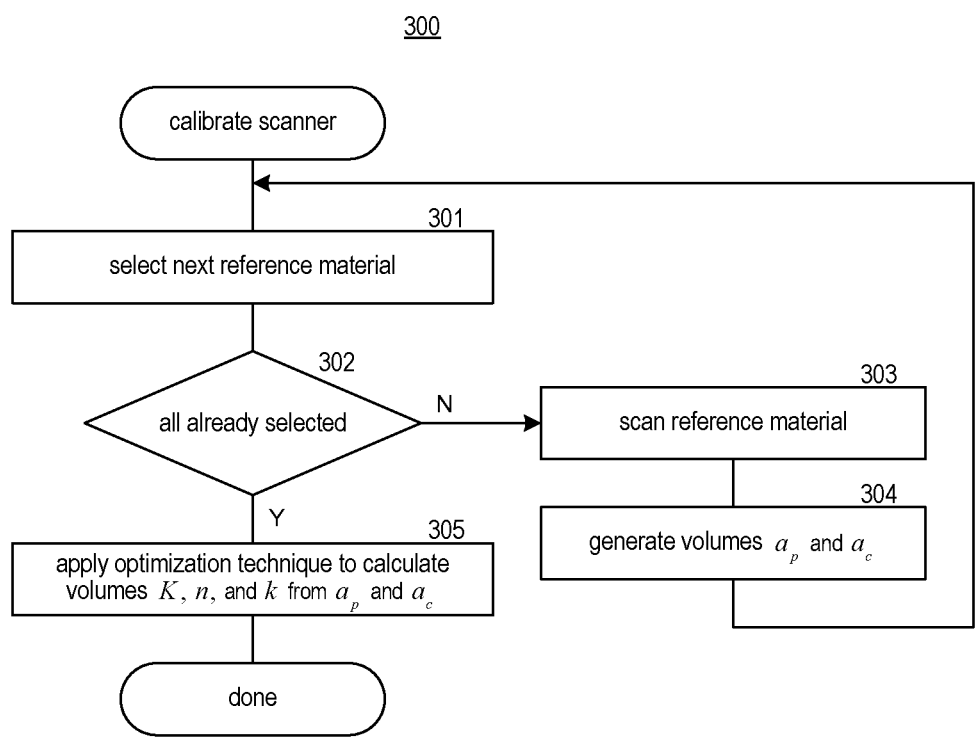
FIG. 3 is a flow diagram that illustrates the processing of a calibrate scanner component in some embodiments.

FIG. 3 is a flow diagram that illustrates the processing of a calibrate scanner component in some embodiments. A calibrate scanner component 300 scans reference materials and generates calibration parameters that best match the reference materials. In block 301, the component selects the next reference material. In block 302, if all the reference materials have already been selected, then the component continues at block 305, else the component continues at block 303. In block 303, the component directs the scanning of the reference material. In block 304, the component generates a photoelectric component volume $a_p$ and a Compton component volume $a_c$ for the scanned reference material and loops to block 301 to select the next reference material. The reference materials may also be scanned together during a single scan, in which case the generation of the $a_p$ and $a_c$ volumes could also be done simultaneously. In block 305, the component applies an optimization technique to calculate the calibration parameters that best match the photoelectric component volumes $a_p$ and the Compton component volumes $a_c$ to the $(\rho_e, Z_e)$ of the reference materials.

Figure 4:
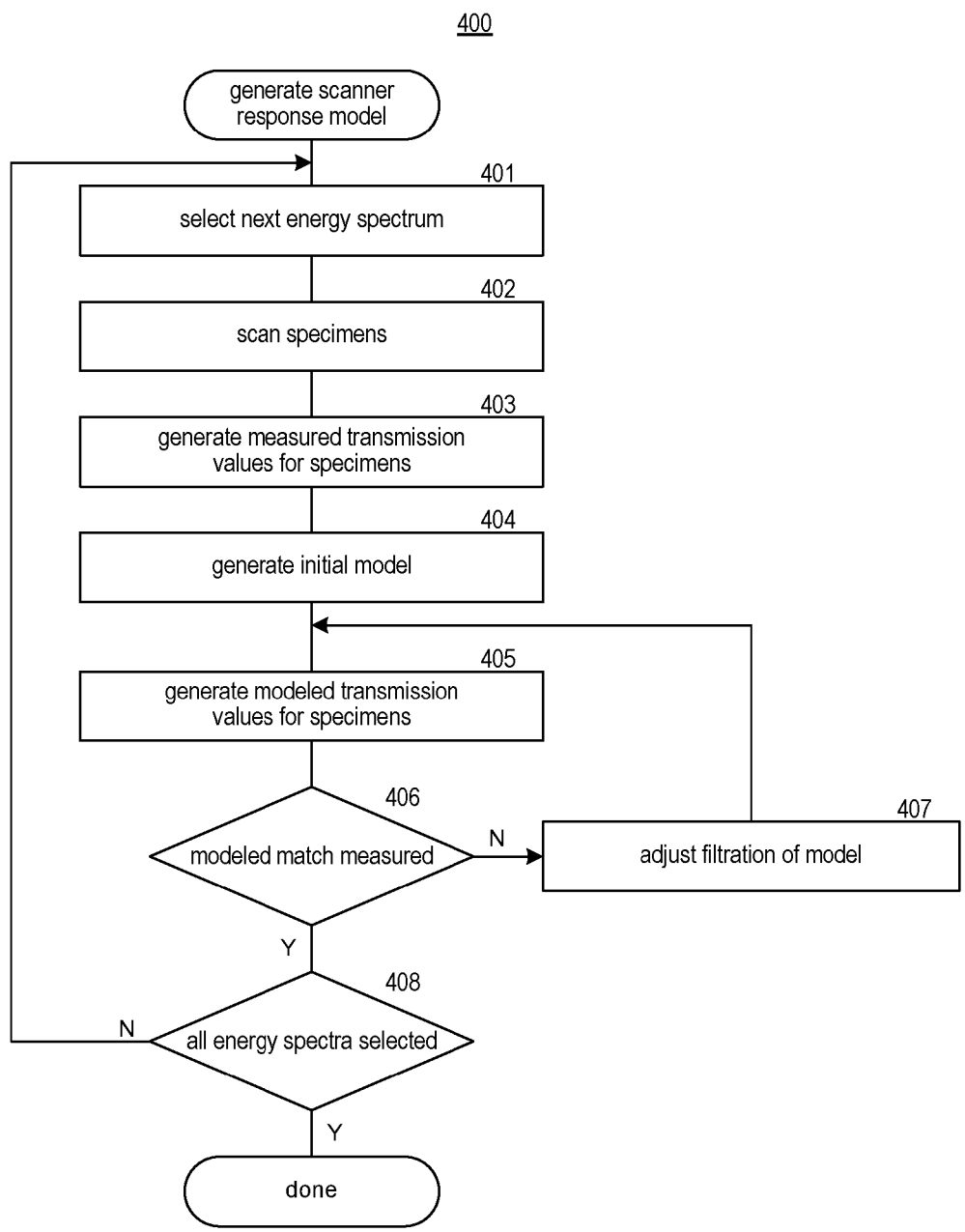
FIG. 4 is a flow diagram that illustrates the processing of a component that generates a scanner spectral response model in some embodiments.

FIG. 4 is a flow diagram that illustrates the processing of a component that generates a scanner spectral response model in some embodiments. A generate scanner spectral response component 400 generates an initial model for each spectral energy distribution of a scanner spectral response based on manufacturer specifications and iteratively refines each model until each model generates transmission values that match measured transmission values for a set of well characterized specimens. In block 401, the component selects the next spectral energy distribution to be modeled. In block 402, the component directs the scanning of various spectral model calibration specimens using the selected source settings. In block 403, the component generates measured transmission values for these specimens in relation to estimated chord length. In block 404, the component generates an initial model for the scanner. In blocks 405-407, the component loops, adjusting the filtration component of the model until the modeled transmission values match the measured transmission values. In block 405, the component generates modeled transmission values for the specimen materials. In decision block 406, if the modeled transmission values match the measured transmission values, then the component continues at block 408, else the component continues at block 407. In block 407, the component adjusts the filtration of the model and loops to block 405 to generate revised modeled transmission values. In decision block 408, if all the energy spectral energy distributions have been selected, then the component completes, else the component continues at block 401 to select the next spectral energy distribution.

The SIRZ system may be employed in various applications to characterize the material within an object. For example, the SIRZ system may be used to process DECT scans of baggage at an airport to characterize bags or in characterization of tissue composition and identification in medical scans. The system may be used systems with endpoint energy from 50-300 keV, characterizing materials with $Z_e$ between 6 and 20.

The following paragraphs describe various embodiments of aspects of the SIRZ system. An implementation of the SIRZ system may employ any combination of the embodiments. The processing described below may be performed by a computing device with a processor that executes computer-executable instructions stored on a computer-readable storage medium that implements the SIRZ system.

In some embodiments, a method for characterizing material of an object scanned via a dual-energy computed tomography scanner is provided. The method receives a low-energy sinogram and a high-energy sinogram based on a scan of the object. The method generates photoelectric and Compton sinograms based on a photoelectric-Compton decomposition of the low-energy sinogram and the high-energy sonogram, and based on a scanner spectral response model. The method generates a photoelectric volume indicating a photoelectric attenuation coefficient for each voxel within a volume representing the object based on the photoelectric sinogram. The method generates a Compton volume indicating a Compton attenuation coefficient for each voxel within the volume representing the object based on the Compton sinogram. For at least some of the voxels of the volume, the method generates an estimated electron density based on the Compton coefficient for the voxel and a scanner-specific electron density calibration parameter and generates an estimated effective atomic number based the photoelectric coefficient and the Compton attenuation coefficient for the voxel and a scanner-specific atomic number calibration parameter. The method then provides the estimated electron density and estimated effective atomic number as features to be used in characterizing the material within the voxel. In some embodiments, the method generates scanner spectral response models for the scanner by refining filtration of the models until modeled transmissions match measured transmissions for well characterized specimen materials. In some embodiments, the method determines one or more scanner-specific electron density calibration parameters and one or more scanner-specific effective atomic number calibration parameters for a scanner. The method determines the calibration parameters by, for each of a plurality of reference materials, calculating an estimated electron density and an estimated effective atomic number for the reference materials based on a photoelectric attenuation coefficient volume and a Compton attenuation coefficient volume generated from a scan of the reference material by the scanner. The method further determines the calibration parameters by selecting values for the scanner-specific electron density calibration parameters and values for the scanner-specific effective atomic number calibration parameters to fit the estimated electron densities and the estimated effective atomic numbers for the reference materials to reference electron densities and reference effective atomic numbers for the reference materials. In some embodiments, the scanner spectral response models include a low-energy spectral response model of the scanner and a high-energy spectral response model of the scanner. In some embodiments, the identity of a material within a voxel is based on a comparison of the combination of the estimated electron density and the estimated effective atomic number to known electron densities and known effective atomic numbers of known materials. In some embodiments, the estimated electron density for a voxel is the Compton attenuation coefficient for the voxel multiplied by a scanner-specific electron density calibration parameter. In some embodiments, the estimated effective atomic number for a voxel is based on the photoelectric attenuation coefficient for the voxel divided by the Compton attenuation coefficient for the voxel.

In some embodiments, a computing system for estimating the electron density of a material is provided. The computing system comprises a component that generates Compton sinograms based on a photoelectric-Compton decomposition of low-energy sinograms and high-energy sinograms generated from a scan of a volume of the material by a scanner and based on a scanner spectral response model of the scanner. The computing system comprises a component that generates a Compton volume indicating Compton attenuation coefficients for voxels within the volume of the material based on the Compton sinograms. The computing system also comprises a component that, for one or more voxels of the volume, generates an estimated electron density based on the Compton attenuation coefficient for the voxel and a scanner-specific electron density calibration parameter. In some embodiments, the components are stored in a computer-readable storage medium of the computing system and have instructions that are executed by a processor of the computing system. In some embodiments, the computing system further comprises a component that generates photoelectric sinograms based on the low-energy sinograms and the high-energy sinograms and based on the scanner spectral response model of the scanner, a component that generates a photoelectric volume indicating photoelectric attenuation coefficients for voxels within the volume of the material based on the photoelectric sinograms, and a component that, for one or more voxels of the volume, generates an estimated effective atomic number based on a ratio of the photoelectric attenuation coefficient and the Compton attenuation coefficient for the voxel and a scanner-specific effective atomic number calibration parameter. In some embodiments, the computing system further comprises a component that identifies the material within a voxel based on a combination of the estimated electron density and the estimated effective atomic number for the voxel.

In some embodiments, a computing system for estimating the effective atomic number of a material is provided. The computing system comprises a component that generates photoelectric sinograms and Compton sinograms based on a photoelectric-Compton decomposition of low-energy sinograms and high-energy sinograms generated from a scan, by a scanner, of a volume of the material and based on spectral response models of the scanner. The computing system comprises a component that generates a Compton volume indicating Compton attenuation coefficients for voxels within the volume of the material from the Compton sinogram. The computing system comprises a component that generates a photoelectric volume indicating photoelectric attenuation coefficients for voxels within the volume of the material from the photoelectric sinogram. The computing system also comprises a component that, for one or more voxels of the volume, generates an estimated effective atomic number for the voxel based on a ratio of the photoelectric attenuation coefficient and the Compton attenuation coefficient for the voxel and a scanner-specific effective atomic number calibration parameter.

In some embodiments, a computing system for characterizing material of an object is provided. The computing system comprises a component that generates photoelectric sinograms and Compton sinograms based on a photoelectric-Compton decomposition of low-energy sinograms and high-energy sinograms generated from a scan, by a scanner, of a volume of the material and based on a spectral response models of the scanner. The computing system comprises a component that generates a photoelectric volume indicating a photoelectric attenuation coefficient for voxels within a volume representing the object based on the photoelectric sinogram. The computing system comprises a component that generates a Compton volume indicating a Compton attenuation coefficient for voxels within the volume representing the object based on the Compton sinogram. The computing system also comprises a component that identifies a material within a voxel based on a combination of the photoelectric attenuation coefficient for the voxel and the Compton attenuation coefficient for the voxel and scanner-specific calibration parameters. In some embodiments, the component that identifies the material within the voxel generates an estimated electron density for the voxel based on the Compton attenuation coefficient for the voxel and a scanner-specific electron density calibration parameter, generates an estimated effective atomic number based on a ratio of the photoelectric attenuation coefficient and the Compton attenuation coefficient for the voxel and a scanner-specific effective atomic number calibration parameter, and identifies the material within the voxel based on a combination of the estimated electron density and the estimated effective atomic number.

In some embodiments, a method performed by a computing device for generating a spectral response model for a scanner is provided. The method scans reference materials to generate measured transmissions for the reference materials. The method initializes the model for the scanner. The method also refines the model for the scanner by adjusting the filtration of the model until modeled transmissions generated by the model for the reference materials satisfy a matching criterion with the measured transmissions for the reference materials. In some embodiments, the model employs a full electron-photon transport model to simulate energy deposition in a detector of the scanner. In some embodiments, the model is initialized based on specifications for the scanner. In some embodiments, the model is refined by adjusting material and/or thickness of material through which X-rays pass.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims. Accordingly, the invention is not limited except as by the appended claims.

The invention claimed is:

1. A method for characterizing material of an object scanned via a dual-energy computed tomography scanner, the method comprising:
    receiving a low-energy sinogram and a high-energy sinogram based on a scan of the object;
    generating photoelectric and Compton sinograms based on a photoelectric-Compton decomposition of the low-energy sinogram and the high-energy sinogram, and based on a scanner-specific spectral response model, the scanner-specific spectral response model generated by refining filtration of the model until modeled transmissions match measured transmissions for reference materials;
    generating a photoelectric volume indicating a photoelectric attenuation coefficient for each voxel within a volume representing the object based on the photoelectric sinogram;
    generating a Compton volume indicating a Compton attenuation coefficient for each voxel within the volume representing the object based on the Compton sinogram; and
    for voxels of the volume,
        generating an estimated electron density based on the Compton coefficient for the voxel and a scanner-specific electron density calibration parameter;
        generating an estimated effective atomic number based the photoelectric coefficient and the Compton attenuation coefficient for the voxel and a scanner-specific atomic number calibration parameter; and
        providing the estimated electron density and estimated effective atomic number as features to be used in characterizing the material within the voxel.

2. The method of claim 1 further comprising determining one or more scanner-specific electron density calibration parameters and one or more scanner-specific effective atomic number calibration parameters for a scanner by
    for each of a plurality of reference materials, calculating an estimated electron density and an estimated effective atomic number for the reference materials based on a photoelectric attenuation coefficient volume and a Compton attenuation coefficient volume generated from a scan of the reference material by the scanner; and
    selecting values for the scanner-specific electron density calibration parameters and values for the scanner-specific effective atomic number calibration parameters to fit the estimated electron densities and the estimated effective atomic numbers for the reference materials to reference electron densities and reference effective atomic numbers for the reference materials.

3. The method of claim 1 wherein the scanner-specific spectral response model comprises a low-energy spectral response model of the scanner and a high-energy spectral response model of the scanner.

4. The method of claim 1 wherein the identity of a material within a voxel is based on a comparison of the combination of the estimated electron density and the estimated effective atomic number to known electron densities and known effective atomic numbers of known materials.

5. The method of claim 1 wherein the estimated electron density for a voxel is the Compton attenuation coefficient for the voxel multiplied by a scanner-specific electron density calibration parameter.

6. The method of claim 1 wherein the estimated effective atomic number for a voxel is based on the photoelectric attenuation coefficient for the voxel divided by the Compton attenuation coefficient for the voxel.

7. A computing system for estimating the electron density of a material, the computing system comprising:
a component that generates Compton sinograms based on a photoelectric-Compton decomposition of low-energy sinograms and high-energy sinograms generated from a scan of a volume of the material by a scanner and based on a scanner-specific spectral response model of the scanner, the scanner-specific spectral response model generated by refining filtration of the model until modeled transmissions match measured transmissions for reference materials;
a component that generates a Compton volume indicating Compton attenuation coefficients for voxels within the volume of the material based on the Compton sinograms; and
a component that, for one or more voxels of the volume, generates an estimated electron density based on the Compton attenuation coefficient for the voxel and a scanner-specific electron density calibration parameter.

8. The computing system of claim 7 wherein the components are stored in a computer-readable storage medium of the computing system and have instructions that are executed by a processor of the computing system.

9. The computing system of claim 7 further comprising:
a component that generates photoelectric sinograms based on the low-energy sinograms and the high-energy sinograms and based on the scanner-specific spectral response model of the scanner;
a component that generates a photoelectric volume indicating photoelectric attenuation coefficients for voxels within the volume of the material based on the photoelectric sinograms; and
a component that, for one or more voxels of the volume, generates an estimated effective atomic number based on a ratio of the photoelectric attenuation coefficient and the Compton attenuation coefficient for the voxel and a scanner-specific effective atomic number calibration parameter.

10. The computing system of claim 9 further comprising:
a component that identifies the material within a voxel based on a combination of the estimated electron density and the estimated effective atomic number for the voxel.

11. A computing system for estimating the effective atomic number of a material, the computing system comprising:
a component that generates photoelectric sinograms and Compton sinograms based on a photoelectric-Compton decomposition of low-energy sinograms and high-energy sinograms generated from a scan, by a scanner, of a volume of the material and based on a scanner-specific spectral response models of the scanner, the scanner-specific spectral response model generated by refining filtration of the model until modeled transmissions match measured transmissions for reference materials;
a component that generates a Compton volume indicating Compton attenuation coefficients for voxels within the volume of the material from the Compton sinogram; and
a component that generates a photoelectric volume indicating photoelectric attenuation coefficients for voxels within the volume of the material from the photoelectric sinogram; and
a component that, for one or more voxels of the volume, generates an estimated effective atomic number for the voxel based on a ratio of the photoelectric attenuation coefficient and the Compton attenuation coefficient for the voxel and a scanner-specific effective atomic number calibration parameter.

12. A computing system for characterizing material of an object, the computing system comprising:
a component that generates photoelectric sinograms and Compton sinograms based on a photoelectric-Compton decomposition of low-energy sinograms and high-energy sinograms generated from a scan, by a scanner, of a volume of the material and based on a scanner-specific spectral response models of the scanner, the scanner-specific spectral response model generated by refining filtration of the model until modeled transmissions match measured transmissions for reference materials;
a component that generates a photoelectric volume indicating a photoelectric attenuation coefficient for voxels within a volume representing the object based on the photoelectric sinogram;
a component that generates a Compton volume indicating a Compton attenuation coefficient for voxels within the volume representing the object based on the Compton sinogram; and
a component that identifies a material within a voxel based on a combination of the photoelectric attenuation coefficient for the voxel and the Compton attenuation coefficient for the voxel and scanner-specific calibration parameters.

13. The computing system of claim 12 wherein the component that identifies the material within the voxel generates an estimated electron density for the voxel based on the Compton attenuation coefficient for the voxel and a scanner-specific electron density calibration parameter, generates an estimated effective atomic number based on a ratio of the photoelectric attenuation coefficient and the Compton attenuation coefficient for the voxel and a scanner-specific effective atomic number calibration parameter, and identifies the material within the voxel based on a combination of the estimated electron density and the estimated effective atomic number.

14. A method performed by a computing device for generating a spectral response model for a scanner, the method comprising:
accessing measured transmissions for reference materials, the measured transmissions generated by scanning with the scanner the reference materials;
initializing the spectral response model for the scanner; and
refining the spectral response model for the scanner by adjusting filtration of the spectral response model for the scanner until modeled transmissions generated by the spectral response model for the scanner for the reference materials satisfy a matching criterion with the measured transmissions for the reference materials.

15. The method of claim 14 wherein the spectral response model for the scanner employs a full electron-photon transport model to simulate energy deposition in a detector of the scanner.

16. The method of claim 14 wherein the spectral response model for the scanner is initialized based on specifications for the scanner.

17. The method of claim 16 wherein the spectral response model for the scanner is refined by adjusting parameters related to thickness of materials through which X-rays pass.

18. One or more computing systems for generating a scanner-specific spectral response model for a scanner, the one or more computing systems comprising:
   one or more computer-readable storage mediums storing computer-executable instructions for controlling the one or more computing systems to:
      access measured transmissions for reference materials, the measured transmissions generated by scanning with the scanner the reference materials;
      access the scanner-specific spectral response model; and
      refine the scanner-specific spectral response model by adjusting parameters of the scanner-specific spectral response model so that modeled transmissions generated by the scanner-specific spectral response model for the reference materials satisfy a matching criterion with the measured transmissions for the reference materials; and
   one or more processors for executing the computer-executable instructions stored in the one or more computer-readable storage mediums.

19. The one or more computing systems of claim 18 wherein the scanner-specific spectral response model employs a full electron-photon transport model to simulate energy deposition in a detector of the scanner.

20. The one or more computing systems of claim 18 wherein the scanner-specific spectral response model is initialized based on specifications for the scanner.

21. The one or more computing systems of claim 20 wherein the scanner-specific spectral response model is refined by adjusting parameters related to thickness of materials through which X-rays pass.

22. The one or more computing systems of claim 18 wherein the measured transmissions for the reference materials are generated in relation to an estimated chord length.

23. The one or more computing systems of claim 18 wherein the computer-executable instructions further control the one or more computing systems to apply the scanner-specific spectral response model to different energy bands to generate spectral responses.

24. The one or more computing systems of claim 18 wherein the scanner-specific spectral response model is refined by adjusting filtration of the scanner-specific spectral response model.

25. The one or more computing systems of claim 18 wherein the parameters of the scanner-specific spectral response model are adjusted to produce the best fit between the modeled transmissions and the measured transmissions for the reference materials.

26. The one or more computing systems of claim 18 wherein the computer-executable instructions further control the one or more computing systems to periodically generate a new scanner-specific spectral response model to account for a spectral drift of the scanner.

27. The one or more computing systems of claim 18 wherein the scanner-specific spectral response model is initialized based on specifications for the scanner and wherein the scanner-specific spectral response model is refined by adjusting filtration of the scanner-specific spectral response model.

28. The method of claim 1 wherein the scanner-specific spectral response model of the scanner is generated based on transmissions obtained from scans of the reference materials by the scanner.

29. The method of claim 28 wherein the scanner-specific spectral response model of the scanner is further based on experimentally measured transmissions for the reference materials.

30. The method of claim 1, wherein the estimated electron density and the estimated effective atomic number are independent of the scanner used to scan the object.

* * * * *